(12) United States Patent
Weber et al.

(10) Patent No.: US 7,795,425 B2
(45) Date of Patent: Sep. 14, 2010

(54) PRODUCTION OF BEPROMOLINE

(75) Inventors: Beat Weber, Zofingen (CH); Stefan Rosenberger, Zofingen (CH)

(73) Assignee: Galderma S.A., Cham (CH)

( * ) Notice: Subject to any disclaimer, the term of this patent is extended or adjusted under 35 U.S.C. 154(b) by 330 days.

(21) Appl. No.: 12/010,635

(22) Filed: Jan. 28, 2008

(65) Prior Publication Data

US 2008/0269483 A1    Oct. 30, 2008

Related U.S. Application Data

(63) Continuation of application No. PCT/IB2006/003362, filed on Jul. 27, 2006.

(30) Foreign Application Priority Data

Jul. 28, 2005    (EP) .................................. 05291611

(51) Int. Cl.
C07D 265/30    (2006.01)
(52) U.S. Cl. .................................................... 544/106
(58) Field of Classification Search .................. 544/106
See application file for complete search history.

(56) References Cited

U.S. PATENT DOCUMENTS

| 3,046,280 A | 7/1962 | Kralt et al. |
| 4,202,894 A | 5/1980 | Pfiffner |
| 4,283,534 A | 8/1981 | Goetz et al. |

FOREIGN PATENT DOCUMENTS

| EP | 0 024 334 | 3/1981 |
| GB | 1 591 267 | 6/1981 |

OTHER PUBLICATIONS

International Search Report PCT/IB2006/003362 dated Feb. 21, 2007.

*Primary Examiner*—Golam M Shameem
(74) *Attorney, Agent, or Firm*—Buchanan Ingersoll & Rooney PC

(57) ABSTRACT

A process for the preparation of a compound of formula (Ia):

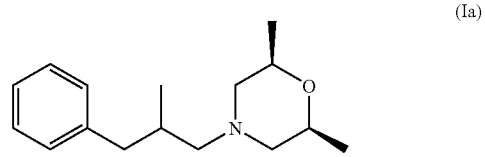

(Ia)

includes: (i) contacting a compound of formula (III):

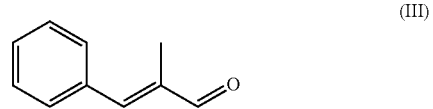

(III)

with a compound of formula (IV):

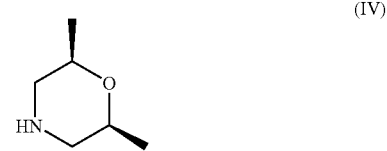

(IV)

in the presence of a palladium catalyst, methanol and hydrogen gas, the step (i) preferably being conducted under basic conditions with acetic acid being added to the medium of reaction once the consumption of the hydrogen gas has ceased.

5 Claims, No Drawings

PRODUCTION OF BEPROMOLINE

CROSS-REFERENCE TO PRIORITY/PCT APPLICATIONS

This application claims priority under 35 U.S.C. §119 of EP 05291611.1, filed Jul. 28, 2005, and is a continuation of PCT/IB 2006/003362, filed Jul. 27, 2006 and designating the United States (published in the English language on Feb. 1, 2007 as WO 2007/012984 A2), each hereby expressly incorporated by reference in its entirety and each assigned to the assignee hereof.

BACKGROUND OF THE INVENTION

1. Technical Field of the Invention

The present invention relates to an improved process of producing bepromoline hydrochloride (bepromoline HCl), which is an intermediate used in the production of Amorolfine (AMF) hydrochloride (Amorolfine HCl).

Amorolfine HCl is an active pharmaceutical ingredient (API) formulated into topical anti-mycotic (anti-fungal) compositions.

2. Description of Background and/or Related and/or Prior Art

French Patent No 2,463,767 describes methods of producing Amorolfine HCl and intermediates for such production. In particular, a method for the production of bepromoline base of formula (Ia):

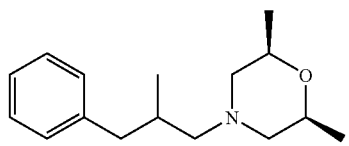
(Ia)

is described, this method involving the step of reacting a compound of the formula (III):

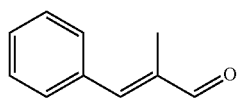
(III)

with a compound of the formula (IV):

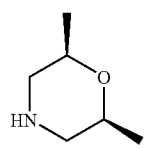
(IV)

such that they undergo catalytic hydrogenation to produce bepromoline base. The suggested catalysts are those generally employed for hydrogenation, with specific mention of platinum, palladium, palladiumcarbon or Raney nickel catalysts. No indication is made of the pH of the hydrogenation conditions.

Need continues to exist for improved processes for the production of Amorolfine salts, for example Amorolfine HCl, notably through an improvement in the production of its intermediates, such as bepromoline or a salt of bepromoline as, for example, bepromoline HCl.

As employed herein, the term "bepromoline base" refers to the compound of formula (Ia), the term "bepromoline HCl" refers to the compound of formula (Ib), and the term "Amorolfine HCl" (AMF HCl) refers to the compound of formula (II):

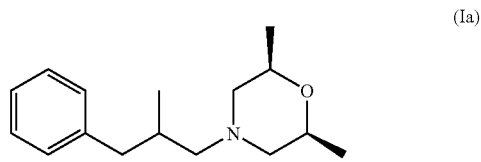
(Ia)

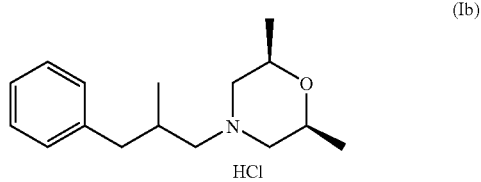
(Ib)

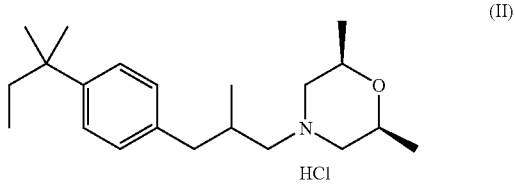
(II)

SUMMARY OF THE INVENTION

The present invention relates to an improved process for producing bepromoline HCl, an intermediate in the production of AMF HCl.

According to a first embodiment of the invention, there is provided a process of preparing bepromoline base, which is a compound of formula (Ia):

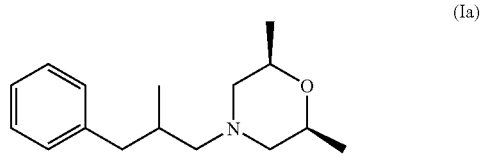
(Ia)

said process comprising:

(i) contacting a compound of formula (III):

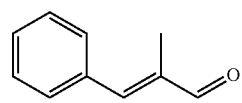
(III)

with a compound of formula (IV):

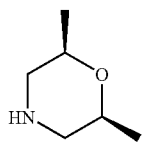

in the presence of a palladium catalyst, methanol and hydrogen gas, wherein (ii), once the consumption of hydrogen gas has ceased, acetic acid is added.

This acetic acid addition (step (ii)) is for the reduction of the C=N double bond under hydrogen pressure.

DETAILED DESCRIPTION OF BEST MODE AND SPECIFIC/PREFERRED EMBODIMENTS OF THE INVENTION

More preferably, step (i) is conducted under basic conditions and acetic acid added once the consumption of hydrogen gas has ceased.

The reduction under hydrogen pressure of the C=C double bond is better conducted under basic conditions (step (i)), and once the consumption of hydrogen gas has ceased, the reduction under hydrogen pressure of the C=N double bond is better conducted under acetic conditions (step (ii)).

Consequently, a preferred process according to the invention is a process of preparing bepromoline base, which is a compound of formula (Ia):

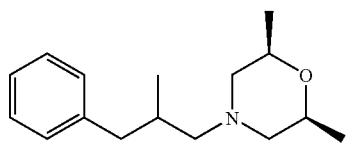

said process comprising:
(i) contacting a compound of formula (III):

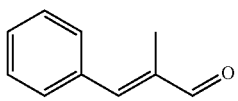

with a compound of formula (IV):

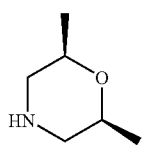

in the presence of a palladium catalyst, methanol and hydrogen gas, wherein step (i) is conducted under basic conditions, and (ii), once the consumption of hydrogen gas has ceased, acetic acid is added.

Compounds of formulae (III) and (IV) are termed herein "α-methylcinnamaldehyde" and "cis-2,6-dimethyl morpholine" (DMM), respectively.

In one embodiment, the palladium catalyst comprises palladium precipitated onto carbon.

Typically, the basic conditions are provided by potassium hydroxide, although other alkalis can also be used. It has been found that the inclusion of 1.5 to 2.0 mol % potassium hydroxide, typically about 1.8 mol % potassium hydroxide, is sufficient.

Generally, the compounds of formulae (III) and (IV) are added in approximately equimolar proportions.

According to a second embodiment of the present invention, there is provided a process for preparing a compound of formula (Ib):

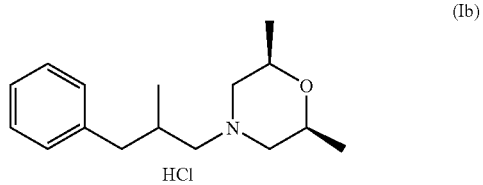

said process comprising a process described above for the first embodiment of the invention followed by the following step: (iii) contacting the compound of formula (Ia) with toluene and HCl gas to produce a compound of formula (Ib).

In one embodiment, the toluene and HCl gas are added at a temperature of up to 50° C.

In another embodiment, the process of preparing a compound of formula (Ib) includes one or more of the following steps:

(a) purifying the compound of formula (Ia);
(b) adding fresh toluene and HCl gas;
(c) adjusting the pH to 3 to 4;
(d) cooling to 0 to 5° C.;
(e) stirring for at least 1 hour; and
(f) isolating the end product of formula (Ib).

In another embodiment, step (a) entails:

(a1) filtering and washing the catalyst with methanol and water;
(a2) removing any used methanol;
(a3) adding toluene and extracting inorganic components using water; and
(a4) removing used toluene and unreacted DMM.

According to the present invention, the solubilization of the compound of formula (Ia) in toluene followed by acidification with hydrochloric acid are particularly useful, because this step avoids distillation of the compound of formula (Ia), which is long-time consuming. Moreover, the solid hydrochloride salt of formula (Ib) obtained in toluene is easier to handle than the liquid compound of formula (Ia) and can be directly employed in the following reaction.

According to a third embodiment of the present invention, there is provided a process of preparing a compound of formula (V):

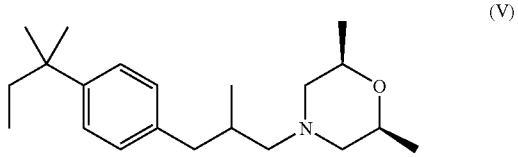

said process comprising a process described above for any of the first, or second embodiment of the present invention.

Compounds of formula (V) are termed herein "Amorolfine base" (AMF base).

For example, in order to obtain Amorolfine base, bepromoline HCl (compound (Ib)) can be contacted with, for example, $FeCl_3$, and then added to 2-chloro-2-methylbutane.

For example, in order to obtain Amorolfine base, bepromoline base (compound (Ia)) can be converted to bepromoline HCl by a salification step, and then submitted to the same reactions as herein above described (contact with for example $FeCl_3$, and then addition to 2-chloro-2-methylbutane).

Typically, the process of the third embodiment further includes the step of reacting a compound of formula (Ib) with 2-chloro-2-methylbutane in the presence of $FeCl_3$ as Friedel-Crafts catalyst.

The Friedel-Crafts catalyst will usually be embodiment in a suitable solvent, for example dichloromethane (DCM).

Typically, the compound of formula (Ib) is contacted with the Friedel-Crafts catalyst at room temperature.

Usually, the 2-chloro-2-methylbutane is added to the compound of formula (Ib) at a temperature of −40° C. to −60° C., for example −50° C.

According to a fourth embodiment of the present invention, there is provided a process for preparing a compound of formula (II) (AMF HCl), said process comprising the process of any of first, second, or third embodiments of the invention.

In one embodiment, the process for preparing a compound of formula (II) further comprises the step of crystallizing AMF HCl from addition of HCl to a solution of AMF base in ethanol.

Typical and usual features of each embodiment of the invention are as for each of the other embodiments of the invention mutatis mutandis.

Finally, the present invention features the compound of formula (Ib) (bepromoline HCl):

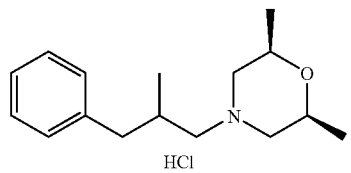

as such, which is produced according to the process as described in the second embodiment of the invention.

The present invention also features the compound of formula (Ia) (bepromoline base) or to compound of formula (Ib) (bepromoline HCl), each of these compounds having a purity degree superior or equal to 99.5%.

Throughout the specification, unless the context demands otherwise, the terms "comprise" or "include", or variations such as "comprising" and "including" will be understood to imply the inclusion of a stated feature, or group of features, but not to the exclusion of any other feature, or group of features.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Production of Bepromoline HCl a) General Considerations:

A mixture of one part of α-methyl-cinnamaldehyde to one part of cis-2,6-dimethyl-morpholine (DMM) is hydrogenated in methanol in the presence of catalytic amount of palladium on carbon, optionally under basic conditions until the uptake of $H_2$ gas ceases, this indicating completion of the reduction of the C═C double bond. Acetic acid is then added for the reduction of the C═N double bond under hydrogen pressure; the C═N double bond is formed between the aldehyde and the amino moiety of the two reactants, α-methyl-cinnamaldehyde and DMM, respectively.

The catalyst is then filtered off and the methanol is removed by distillation. Toluene is added and the inorganic components are removed by washing with water. Toluene and unreacted DMM are distilled off. Then fresh toluene and HCl gas are added and the pH is adjusted to 3-4. The bepromoline HCl is centrifuged and dried.

Schematic of Production of Bepromoline HCl:

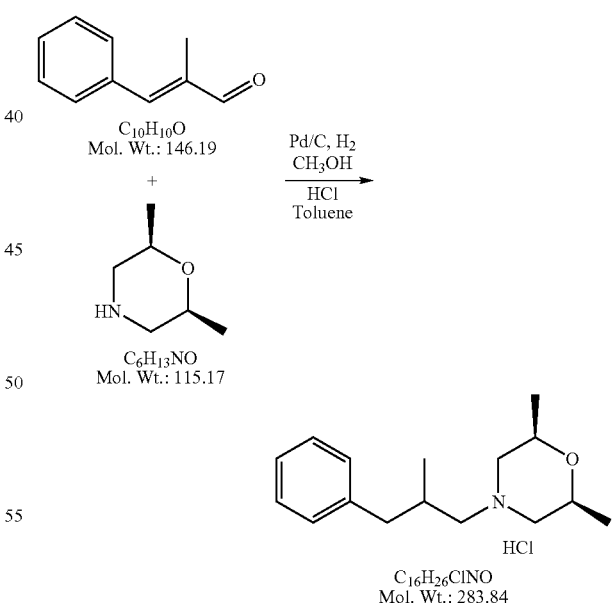

Provision of Basic Conditions:

Basic conditions were provided by KOH, which is used to neutralize the acidic components present in the α-methyl-cinnamaldehyde. The absence of traces of acid improved the kinetics of the reaction. The reduction of the aldehyde function to the corresponding alcohol is avoided by addition of KOH.

Solvent:

Methanol may be substituted by toluene to avoid the later solvent exchange step.

Temperature of Hydrogenation:

40° C. is the optimum temperature for both hydrogenation steps. However, the temperature may typically be set at no more than 45° C., preferably between 30° C. and 45° C.

Acetic Acid:

The reduction for the C=N double bond formed between the aldehyde and the amino function of the two components is conducted under hydrogen pressure in acidic conditions after the addition of acetic acid.

A molar ratio of acetic acid to KOH is around 1.3 (±10%).

The acetic acid is typically added at a temperature range of between 40° C. to 45° C., and no more than 45° C.

Toluene Exchange:

The toluene is advantageously added to facilitate the phase separations and the distillation step of the unreacted DMM, thus improving the purity of bepromoline.

Bepromoline HCl purity:

The trans isomers (VI) and (VII) of bepromoline, coming from trans isomers presents as byproducts in the 2,6-dimethyl morpholine starting material, are partially eliminated during the crystallization of bepromoline HCl.

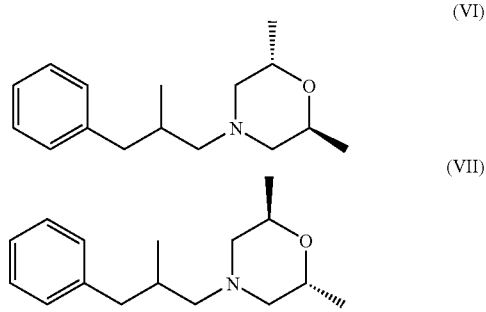

The purity of the bepromoline HCl (cis isomer) is superior or equal to 99.5%.

Stability Temperature:

The product is stable up to 150° C.

b) Synthesis: (Weights are given for 1 kmol α-methyl-cinnamaldehyde).

A reactor was charged with 146 kg α-methyl-cinnamaldehyde, 115 kg cis-2,6-dimethyl-morpholine, 2.1 kg 50% KOH, 278 kg methanol and 5.8 kg of a palladium/carbon catalyst and then filled with hydrogen at 15-25° C.

The hydrogenation was then conducted at a pressure of ~2 bar and 35-45° C. until $H_2$ consumption ceased.

1.5 kg acetic acid was then added, and the hydrogenation was re-commenced. The hydrogenation was conducted at a pressure of ~2 bar and at a temperature of 40-45° C. until no further $H_2$ was consumed.

The reaction mixture was filtered and the catalyst washed with methanol and water.

The solvents were distilled off at a temperature of up to 95° C. under vacuum.

Two extractions were performed using toluene and water. The waste water was drained off.

The solvent was then distilled off under vacuum.

The reactor was charged with 904 kg toluene and 33 kg HCl gas at a temperature of up to 50° C. Then the pH was adjusted to 3-4. The reaction mixture was cooled and then stored sufficiently to reached complete crystallization.

The mixture was centrifuged and washed with cold (0-5° C.) toluene. A second crop of Bepromoline HCl was isolated from the mother liquor.

The process yielded 287 kg wet bepromoline HCl, which was then dried at 60° C. under vacuum. After drying, the first crop of Bepromoline HCl was 227 kg and the second 18 kg. This corresponds to a yield of 87% (80% for the first crop Bepromoline HCl and 7% for the second crop).

Example 2

Production of Amorolfine Base a) General Considerations:

1 part bepromoline HCl is treated with 1.3 parts $FeCl_3$±5% in dichloromethane at room temperature. The resulting slurry is cooled to approximately −50° C., whereupon 1 to 1.1 parts of 2-chloro-2-methylbutane is added.

After an appropriate reaction time of around 2.5 hours, the reaction mixture is poured onto an ice-water mixture. The organic phase is separated and washed with acidic water, and then with sodium phosphate solution and with sodium hydroxide solution. After a stripping with toluene, extractions with water are performed. The solvent is then removed. Then the residue is distilled.

Schematic of Production of Amorolfine Base:

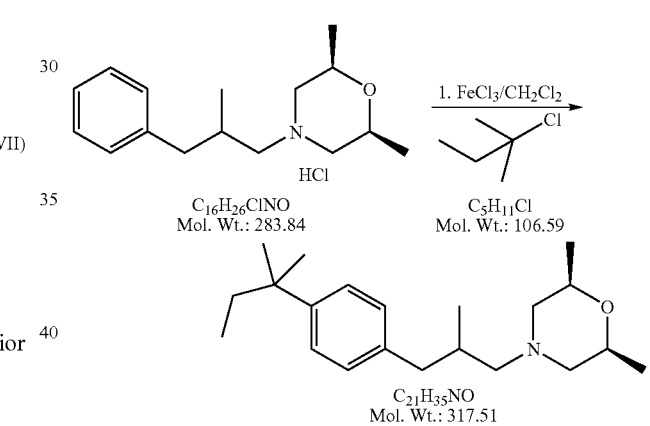

Reaction Temperature for the addition of $FeCl_3$ to Bepromoline HCl:

The addition of $FeCl_3$ to Bepromoline HCl takes place at room temperature. At lower temperatures the subsequent Friedel-Crafts alkylation fails partially or completely (Table 1).

TABLE 1

| Temperature(° C.) | Bepromoline assay in the crude Amorolfine base(%) |
|---|---|
| 20-30 | 8-14 |
| 0 | 14 |
| −20 | 100 |

Friedel-Crafts Catalysts:

A suitable molar ratio of $FeCl_3$ to bepromoline is 1:2 to 1:5 equivalents of catalyst. 1.3 equivalents of $FeCl_3$ are preferred.

Reaction Temperature for Friedel-Crafts Alkylation:

To decrease the Fenpropimorph (FPM) byproduct, the reaction is conducted at low temperature, preferably −50° C. (see Table 2):

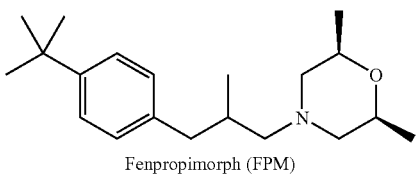

Fenpropimorph (FPM)

TABLE 2

| Temperature(° C.) | FPM(%) |
|---|---|
| −52 to −49 | 0.14-0.25 |
| −40 | 1.7 |
| −35 | 2.0 |
| −20 | 2.7 |

Fenpropimorph (FPM) is a problematic byproduct as it is difficult to remove from the end product.

Ratio of Bepromoline HCl to 2-chloro-2-methylbutane:

Batches were performed with 10% excess 2-chloro-2-methylbutane and at a 1:1 ratio. The FPM assay is lower for the 1:1 ratio and thus this proportion is preferred.

Phosphate and Alkaline Extraction:

The Amorolfine HCl (which is in the DCM) is converted to the free base during these extractions. Phosphate was used to remove traces of Fe.

Solvent Exchange:

Advantages result if the solvents are exchanged (i.e., toluene in place of DCM): the volume is reduced and the wastewater is contaminated with less chlorinated solvent.

Toluene-water Extraction:

These extractions are necessary to get the appropriate quality for the subsequent distillation. If these extractions are omitted, the Amorolfine base slightly decomposes at 180° C. The distillation becomes very sluggish and fumes are formed. The vacuum distillation is then not possible at plant scale.

The yield was approximately 90% of crude Amorolfine base.

b) Synthesis: (weights are given for 1 kmol bepromoline HCl).

The reactor was charged with 212 kg $FeCl_3$ and 757 kg DCM. 284 kg bepromoline HCl in 946 kg DCM were added to the reactor at 20-30° C. The reaction mixture was completed with 213 kg DCM and cooled to −50° C. 107 kg 2-chloro-2-methylbutane in 107 kg DCM were added at −50° C., although a temperature of −60 to −45° C. is acceptable, and stirred for 2.5 hours.

Hydrolysis was performed using 255 kg ice and 785 kg water.

Phase separation was then performed.

Extractions using slightly acidic water (water and diluted HCl) were performed, followed by a further extraction with a solution of $Na_3PO_4$ in water. A subsequent extraction was conducted using NaOH diluted in water to a pH≧13. At a lower pH value there is incomplete HCl removal, leading to distillation problems. Two washes were performed with water.

The solvent was distilled off.

Toluene was added and water extractions were performed. Finally the solvent was distilled off under vacuum.

This yielded 283 kg crude AMF (approximately 90% AMF base crude)

Example 3

Distillation of Amorolfine Base a) General Considerations:

The distillation step is necessary to purify Amorolfine Base.

Schematic of the Distillation Process:

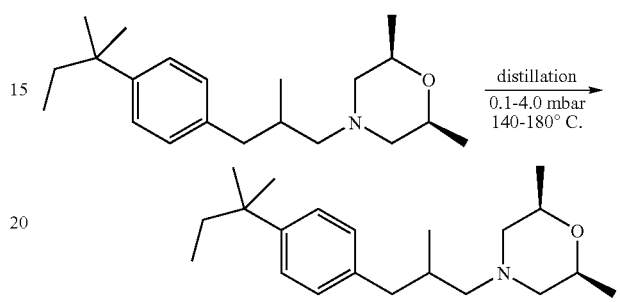

b) Distillation:

283 kg of crude Amorolfine base are distilled at 141°-144° C. under reduced pressure (typically 0.14-0.15 mbar). The fractions are combined in such a way that the impurity profile of the combined material is within the desired specification.

After distillation, 190 kg AMF base were produced (approximately 67% AMF base distilled).

Example 4

Production of Amorolfine HCl and Evaluation of the Purity of the Produced Compound a) General Considerations:

i) Purpose: The goal of this stage is to ensure that sufficient impurities are properly removed with the formation of the Amorolfine HCl and only one crystallization step with ethanol being used.

ii) production of Amorolfine HCl with Amorolfine base (salification step): HCl gas is added to a solution of Amorolfine base in two parts of ethanol until the pH reaches 1.5 to 3. The Amorolfine HCl crystallizes at around 45° C. The slurry is cooled to no less than −15° C. (which should take no less than 2 hours). The crude Amorolfine HCl is isolated by centrifugation and washed with cold ethanol. The crude Amorolfine HCl is then recrystallized from two parts of ethanol.

Schematic of the Process:

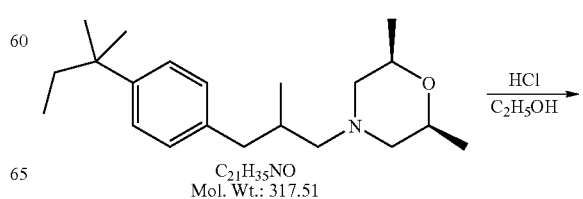

$C_{21}H_{35}NO$
Mol. Wt.: 317.51

-continued

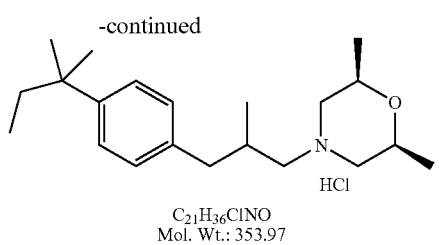

C₂₁H₃₆ClNO
Mol. Wt.: 353.97

Amounts of byproducts in the Amorolfine base:

Apart from FPM, all impurities present in AMF base are removed firstly by the salification of AMF base into AMF HCl and secondly by one crystallization step from ethanol.

The data given in Table 3 were taken from different crystallization experiments.

TABLE 3

|  | Bepromoline(%) | FPM(%) | Trans-isomers(%) |
|---|---|---|---|
| AMF base | 5 | 0.25 | 0.5 |
| AMF HCl crude | 0.3 | 0.25 | 0.3 |
| AMF HCl | <0.1 | 0.25 | <0.2 |
| Required spec. | <0.2 | <0.3 | <0.2 |

Reaction Temperature:

During the addition of the HCl gas, the temperature raises by around 35° C. This exotherm is used to warm the batch. After the addition of HCl the temperature is raised to a level that ensures that the reaction mixture is in solution.

The final temperature of −20 to −15° C. is important to obtain an optimum yield.

Recrystallization of the Amorolfine HCl:

Ethanol is the preferred solvent. The Amorolfine HCl is dissolved in hot ethanol and this solution is filtered to remove foreign matter. The filtrate is then cooled to −15 to −20° C. to get the optimum yield of crystallization. After centrifugation, the crystals are washed with an appropriate amount of ethanol.

Drying:

The Amorolfine HCl is stable up to 150° C. Drying conditions of 60° C. in a vacuum are used and do not 25 produce any problems with the residual solvent.

b) Synthesis: (Weights are given for 1 kmol AMF base).

The reactor was charged with 317 kg AMF and 640 kg ethanol. 38 kg HCl gas was added at 10-65° C. The reaction mixture was then heated to 60° C., followed by cooling to −15 to −20° C. The mixture was stored for 30 minutes to 2 hours.

The Amorolfine HCl was centrifuged and washed with 210 kg of ethanol.

2 parts ethanol were used to dissolve the Amorolfine HCl at 70-80° C.

The hot solution was filtered and the filter rinsed with 15 kg hot ethanol. The filtrate was then cooled to −15 to −20° C. and stored for 30 minutes to 2 hours.

The crystallized Amorolfine HCl was centrifuged and washed with 210 kg of ethanol.

The mixture was then dried at a temperature of 60° C. under vacuum (<100 mbar).

This yielded 271 kg AMF HCl. The yield was approximately 77%.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a compound of formula (Ia):

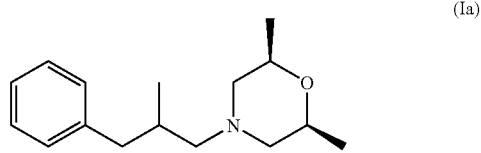

said process comprising:
(i) contacting a compound of formula (III):

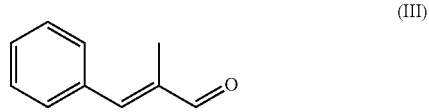

with a compound of formula (IV):

in the presence of a palladium catalyst, methanol and hydrogen gas, wherein (ii), once the consumption of hydrogen gas has ceased, acetic acid is added to the medium of reaction.

2. The process as defined by claim 1, wherein step (i) is conducted under basic conditions.

3. The process as defined by claim 2, wherein said basic conditions are provided by potassium hydroxide.

4. The process as defined by claim 1, wherein the compounds of formulae (III) and (IV) are employed in essentially equimolar proportions.

5. The process as defined by claim 1, the catalyst comprising palladium precipitated onto carbon.

* * * * *